US008741174B1

(12) United States Patent
Tucker

(10) Patent No.: US 8,741,174 B1
(45) **Date of Patent: *Jun. 3, 2014**

(54) REDUCED WEIGHT DECONTAMINATION FORMULATION FOR NEUTRALIZATION OF CHEMICAL AND BIOLOGICAL WARFARE AGENTS

(75) Inventor: Mark D. Tucker, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 1114 days.

This patent is subject to a terminal disclaimer.

(21) Appl. No.: 12/124,191

(22) Filed: May 21, 2008

Related U.S. Application Data

(63) Continuation-in-part of application No. 10/251,569, filed on Sep. 20, 2002, now Pat. No. 7,390,432.

(51) Int. Cl.

| | |
|---|---|
| *A62D 3/00* | (2007.01) |
| *A62D 9/00* | (2006.01) |
| *C01B 15/01* | (2006.01) |
| *C09K 3/00* | (2006.01) |
| *C11D 3/39* | (2006.01) |
| *C01B 7/00* | (2006.01) |
| *C01B 15/00* | (2006.01) |
| *A01N 39/00* | (2006.01) |
| *A61K 33/40* | (2006.01) |
| *C11D 17/00* | (2006.01) |
| *C12N 9/24* | (2006.01) |

(52) U.S. Cl.
USPC ............ 252/186.41; 252/186.39; 252/186.38; 252/186.4; 424/616; 435/200; 510/444

(58) Field of Classification Search
USPC ............... 252/186.41, 186.4, 186.38, 186.39; 424/616; 435/200; 510/444
See application file for complete search history.

(56) References Cited

U.S. PATENT DOCUMENTS

| | | | | |
|---|---|---|---|---|
| 5,356,803 | A * | 10/1994 | Carpenter et al. | 435/200 |
| 5,512,206 | A * | 4/1996 | Steltenkamp et al. | 252/186.4 |
| 5,582,627 | A * | 12/1996 | Yamashita | 71/26 |
| 6,093,688 | A * | 7/2000 | Gordon | 510/224 |
| 6,235,703 | B1 * | 5/2001 | Appel et al. | 510/444 |
| 6,436,445 | B1 * | 8/2002 | Hei et al. | 424/667 |
| 6,569,353 | B1 * | 5/2003 | Giletto et al. | 252/186.28 |
| 2004/0022867 | A1 * | 2/2004 | Tucker et al. | 424/616 |

OTHER PUBLICATIONS

Abstract of Adams et al. Acta Crystallographica 1977 B33 p 3650. pdf.*
20 Mule Team MSDS Potassium Tetraborate {US Borax May 2000}.*

* cited by examiner

*Primary Examiner* — Patrick Ryan
*Assistant Examiner* — Aaron Greso
(74) *Attorney, Agent, or Firm* — Daniel J. Jenkins

(57) ABSTRACT

A reduced weight DF-200 decontamination formulation that is stable under high temperature storage conditions. The formulation can be pre-packed as an all-dry (i.e., no water) or nearly-dry (i.e., minimal water) three-part kit, with make-up water (the fourth part) being added later in the field at the point of use.

11 Claims, 3 Drawing Sheets

REDUCED WEIGHT DECONTAMINATION FORMULATION FOR NEUTRALIZATION OF CHEMICAL AND BIOLOGICAL WARFARE AGENTS

CROSS-REFERENCE TO RELATED APPLICATIONS

This application is a continuation-in-part application of U.S. patent application Ser. No. 10/251,569, entitled "Enhanced Formulations for Neutralization of Chemical, Biological and Industrial Toxants", filed on Sep. 20, 2002, now U.S. Pat. No. 7,390,432, and the specification thereof is incorporated herein by reference.

FEDERALLY SPONSORED RESEARCH

The United States Government has rights in this invention pursuant to Department of Energy Contract No. DE-AC04-94AL85000 with Sandia Corporation.

BACKGROUND OF THE INVENTION

Sandia National Laboratories has previously developed DF-200, an enhanced decontamination formulation for the neutralization of chemical and biological warfare agents and biological pathogens.

Two formulations associated with DF-200 are summarized below:
DF-200HF (Enhanced Formulation for High Foam Applications):
2.0% Variquat 80MC (cationic surfactant)
1.0% Adogen 477 (cationic hydrotrope)
0.4% 1-Dodecanol (fatty alcohol)
2.0% Polyethylene Glycol 8000 (polymer)
0.8% Diethylene Glycol Monobutyl Ether (solvent)
0.5% Isobutanol (solvent)
5.0% Bicarbonate salt (buffer and peroxide activator)
3.5% Hydrogen Peroxide (oxidant)
2.0% Propylene Glycol Diacetate or Glycerol Diacetate (peroxide activator)
10.0% Propylene Glycol (organic stabilizer)
~2.0% Potassium Hydroxide (pH adjustment)
Water (Remainder—~70%)
Note: The formulation can be adjusted to a pH value between 9.6 and 9.9; and is effective for decontamination of all agents tested.
DF-200NF (Enhanced Formulation for No Foam Applications):
2.0% Benzalkonium Chloride
2.0% Propylene Glycol Diacetate or Glycerol Diacetate
3.5% Hydrogen Peroxide
5.0% Potassium Bicarbonate
10.0% Propylene Glycol (organic stabilizer)
~2.0% Potassium Hydroxide
Water (Remainder—~75%)

A new form of the Sandia National Laboratories decontamination formulation (DF-200) is needed to meet the CBW agent decontamination requirements of the US Department of Defense (DOD), and other potential users, for significantly reduced weight and volume burdens. Of primary interest and benefit to the warfighter is the use of one formulation for battlefield and fixed site decontamination that is easily deployable, fast reacting, environmentally friendly with low toxicity and corrosivity properties, and that has a low logistics burden. Currently, the aqueous-based DF-200 is provided in an 'all-liquid' configuration where all water is included within the packaged formulation. Although this configuration of DF-200 makes it simple to use (by quickly mixing each of the three liquid parts) it requires a significant logistics burden since each gallon of the formulation weighs approximately 9 lbs.

A new configuration of the decontamination formulation is needed that can be packaged as a dry kit, with most or all water removed, thereby reducing the packaged weight of the decontamination formulation by ~60% (as compared to the "all-liquid" DF-200 formulation) and significantly lowering the logistics burden on the warfighter. Water (freshwater or saltwater) would be added to the new decontamination formulation configuration at the time of use from a local source.

Currently, standard DF-200 is used by the military in an 'all-liquid' configuration consisting of three parts:
Part A: Foam Component (~49% by volume)—consists of surfactants, solvents, inorganic bases, and buffers dissolved in water;
Part B: 8% Hydrogen Peroxide Solution (~49% by volume)—consists of hydrogen peroxide dissolved in water; and
Part C: Liquid Peroxide Activator (~2% by volume)—consists of an organic liquid.

As seen in the current formulations above, water makes up a substantial portion of DF-200 and, hence, it removal can achieve the desired weight savings. However, development of a reduced weight configuration of DF-200 (i.e., a 'dry' formulation) is a considerable technical challenge. Ideally, a 'dry' formulation would have the following desirable characteristics:
High storage stability in extreme temperature environments
Rapid solubility of the ingredients in both freshwater and saltwater
Low cost (e.g., use of commercially available ingredients)
High efficacy against both chemical and biological warfare agents
Ability to maintain sufficient contact time between the formulation and the agents on both vertical and horizontal surfaces in all deployment conditions
Ability to be easily deployed with existing military equipment To accomplish these objectives, the development of a 'dry' formulation focused on four tasks:
Selection of a liquid or solid hydrogen peroxide material that is stable under high temperature storage conditions.
Selection of hydrogen peroxide materials that can be shipped on commercial aircraft
Development of methods to rapidly dissolve solid peroxide materials in water.
Development of reduced weight formulation components.
Efficacy testing of the reduced weight DF-200 configuration.

SUMMARY OF THE INVENTION

The present invention relates to reduced weight DF-200 decontamination formulations that are stable under high temperature storage conditions. The formulations can be pre-packed as all-dry (i.e., no water) or nearly-dry (i.e., minimal water) three-part kits, with make-up water (the fourth part) being added later in the field at the point of use.

BRIEF DESCRIPTION OF THE DRAWINGS

The accompanying drawings, which are incorporated in and form part of the specification, illustrate various examples of the present invention and, together with the detailed description, serve to explain the principles of the invention.

DETAILED DESCRIPTION OF THE INVENTION

Figure 1:
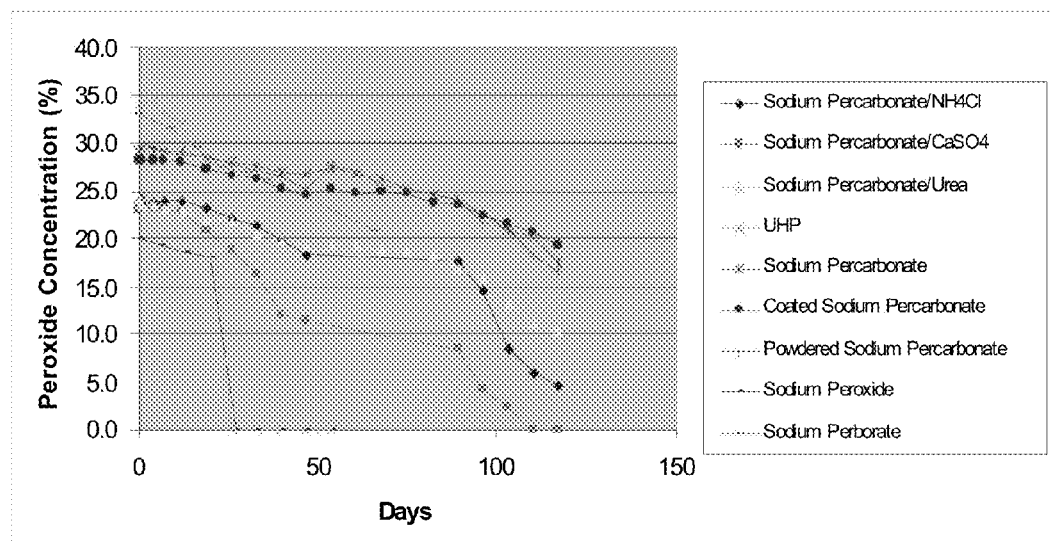
FIG. 1 shows a plot of peroxide concentration versus time.

The use of powdered additives to 'dry-out' some components certain ingredients of standard DF-200 formulations has been described in detail in commonly-owned U.S. Pat. Nos. 7,276,468 and 7,282,470 to Tucker, which are both incorporated herein by reference.

Neutralization is defined as the mitigation, de-toxification, decontamination, or otherwise destruction of TICs to the extent that the TICs no longer cause adverse health effects to humans or animals. The present invention addresses the need for decontamination formulations that are non-toxic, non-corrosive, lost-cost, long shelf-life, and that can be delivered by a variety of means and in different phases, including sprays, foams, fogs, mists, aerosols, gels, creams, pastes, baths, strippable coatings, etc.

The word "formulation" is defined herein as the made-up, "activated" product or solution (e.g., aqueous decontamination solution) that can be applied to a surface or body, or dispersed into the air, etc. for the purpose of neutralization, with or without the addition of a gas (e.g., air) to create foam. Unless otherwise specifically stated, the concentrations, constituents, or components listed herein are relative to the weight percentage of the made-up, activated aqueous decontamination solution. The word "water" is defined herein to broadly include: pure water, tap water, well water, waste water, deionized water, demineralized water, saltwater, or any other liquid consisting substantially of $H_2O$.

A related objective for a reduced weight DF-200 formulation was to identify an alternative solid hydrogen peroxide material (i.e., alternative to urea hydrogen peroxide) that is stable under high temperature storage conditions. The DF-200 technology is based on a low concentration of hydrogen peroxide that works in synergy with other ingredients. One problem with some forms of solid hydrogen peroxide (and other reactive materials) is that they can degrade at elevated temperatures. Therefore, a focus of this development effort has been to identify a form of solid hydrogen peroxide for this application with high stability at elevated temperatures to minimize degradation.

Solid hydrogen peroxide is available in many forms including sodium percarbonate, sodium perborate, peroxymonosulfate, sodium peroxide, and urea hydrogen peroxide. Recently, several peroxide manufacturers have introduced encapsulated forms of these solid peroxide products with claims of high stability properties. A summary of available solid hydrogen peroxide materials is shown in Table 1.

TABLE 1

Summary of solid hydrogen peroxide material properties.

| Material | Peroxide Content (%) | Solubility (%) | Stability | Cost | Comments |
|---|---|---|---|---|---|
| Sodium Perborate Monohydrate | 32 | 2.5 | High | Bulk | |
| Sodium Perborate Tetrahydrate | 24 | 2.5 | High | Bulk | |
| Sodium Percarbonate | 30 | 12 | Med | Bulk | Very slow dissolution rate |
| Urea Hydrogen Peroxide | 37 | >12 | Med | High | |
| Sodium Peroxide | 40 | >12 | High | High | Strongly basic; reacts violently in water |
| Sodium Peroxymonosulfate | 12 | 25 | Med | Bulk | |
| Polymer/Peroxide Complex | 20 | 2 | Low | High | |
| Calcium/ Magnesium Peroxide | 33 | 0.1 | High | Bulk | Dissolves only at pH <2 |

The high temperature stability of various forms of both un-encapsulated and encapsulated solid peroxide compounds have been carefully evaluated to select the most stable form of solid hydrogen peroxide for this application. The thermal properties of the chosen solid peroxides were first assessed using thermogravimetric analysis (TGA) and differential scanning calorimetry (DSC) under an atmosphere of dry air. The decomposition temperature was determined from the onset of a rapid and significant weight loss (>5%) of the sample. The decomposition temperature for each peroxide material is listed in Table 2. All of the solid peroxides, except for urea hydrogen peroxide, had decomposition temperatures well above 100° C. The thermal stability of urea hydrogen peroxide was very poor with an onset of decomposition at 59° C. DSC analysis showed that no thermal events (i.e. melting, mass independent decomposition) occurred prior to the onset of thermal decomposition, as measured by TGA, for each solid peroxide material.

TABLE 2

Thermal analysis of solid peroxides

| Compound, Purity | Decomposition Temperature (° C.)[a] |
|---|---|
| Calcium Peroxide, 75% | >300 |
| Potassium Superoxide, 97% | >300 |
| Sodium Perborate Monohydrate, 95% | 143 |
| Sodium Percarbonate (Provox), 88% | 137 |
| Sodium Percarbonate, Coated (Provox-C), 88% | 137 |
| Sodium Peroxide, 93% | >300 |
| Urea Hydrogen Peroxide, 97% | 59 |
| Zinc Peroxide, 55% | 209 |

[a]Onset of weight loss as measured by TGA

The solubility of the solid peroxide candidates in water was examined next. The DF-200 formulation requires that the solid peroxide be soluble enough to make at least a 3.5 wt % solution. Each solid peroxide material was weighed and dissolved in de-ionized water to theoretically make a 4 wt % solution. The peroxide was stirred in water for 15 min at room temperature, filtered through a 2 μm glass fiber media filter and the filtrate was titrated for hydrogen peroxide content. The results of the solubility tests are shown in Table 3.

TABLE 3

Titrated hydrogen peroxide content. Enough solid peroxide was used to theoretically generate a ~4 wt % solution of hydrogen peroxide.

| Compound, Purity | Titrated wt % $H_2O_2$ |
|---|---|
| Calcium Peroxide, 75% | <0.1 |
| Potassium Superoxide, 97% | 4.8 ± 0.1 |
| Sodium Perborate Monohydrate, 95% | 0.5 ± 0.1 |
| Sodium Percarbonate (Provox), 88% | 4.3 ± 0.1 |
| Sodium Percarbonate, Coated (Provox-C), 88% | 4.4 ± 0.1 |
| Sodium Peroxide, 93% | 4.7 ± 0.1 |
| Urea Hydrogen Peroxide, 97% | 4.4 ± 0.1 |
| Zinc Peroxide, 55% | <0.1 |

Calcium peroxide and zinc peroxide were insoluble in water—no hydrogen peroxide was found by titration. Sodium perborate was slightly soluble, but the hydrogen peroxide content in the solution was significantly lower than what is required for the absorbent/neutralization formulation. All of the other solid peroxides were soluble at a level necessary for the DF-200 formulation to work properly.

Based on these tests, several peroxide materials are considered to be good candidates for this application (i.e., reduced weight, and high temperature stability). These include sodium percarbonate (coated and uncoated) and sodium peroxide. Potassium superoxide was not further evaluated because it reacts violently in water.

Sodium perborate monohydrate initially did not appear to be a viable candidate based on its low solubility. However, work conducted at Sandia as part of this project has identified a method to greatly increase the solubility of this material. This method involves the addition of a second material (e.g., sorbitol, mannitol, etc.) that complexes with the sodium perborate to increase its solubility. Sorbitol, mannitol are inert materials that do not affect the efficacy of the DF-200 formulation. When sodium perborate is dissolved in solution with this secondary material (e.g., sorbitol, mannitol, etc.), its solubility is such that the desired minimum 3.5 wt % peroxide concentration can be achieved. Thus, sodium perborate monohydrate is also considered to be a candidate material.

Next, oven testing was initiated to test the candidate materials. The materials were placed in ovens that cycle between 30° C. and 70° C. on a 24-hour basis. Materials were placed in glass vials with plastic lids. The plastic lids were loosened slightly to provide a mechanism for pressure relief in the vials. Small samples of the peroxide materials were extracted from the oven approximately every three to seven days and the materials were analyzed for peroxide content to determine if any degradation occurred. The results from the first series of oven tests are shown in FIG. 1.

These results show that sodium percarbonate was the most promising material of the materials tested. In the best case, it retained approximately 80% of its original peroxide content even after 120 days of exposure to the high temperature storage conditions. These results also point out that the oven stability tests give dramatically different results than those predicted by the more rapid methods (i.e., thermogravimetric analysis and differential scanning calorimetry). For example, the rapid methods predict that sodium peroxide would be the most stable material. However, in oven testing this material degraded rapidly after approximately 25 days.

Figure 2:
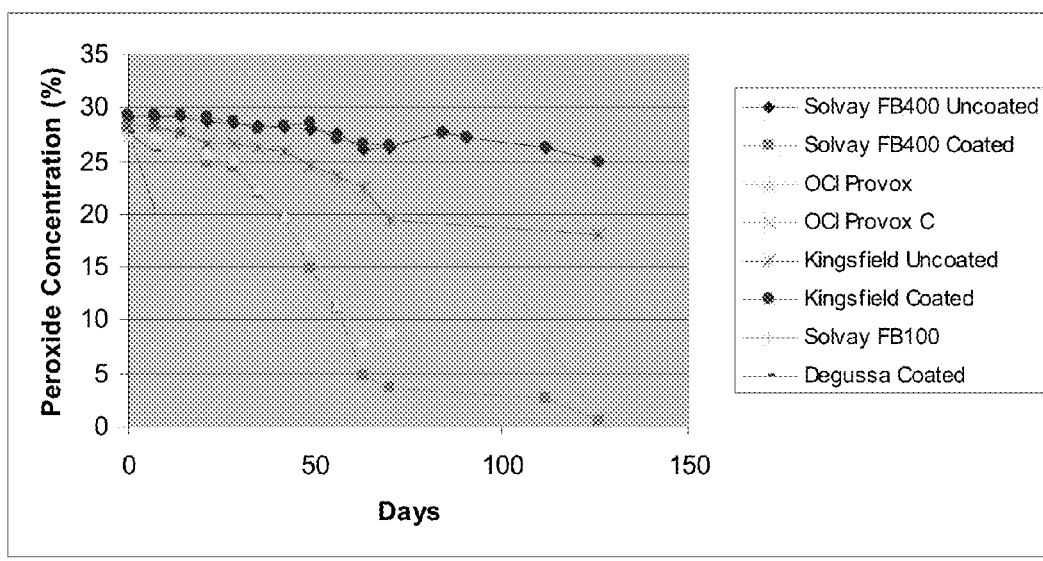
FIG. 2 shows a plot of peroxide concentration versus time.

In the next series of temperature stability tests, sodium percarbonate materials from various manufacturers were collected and tested. The conditions in the oven were the same as in the previous tests. These results are shown in FIG. 2.

These tests demonstrated that two commercial sodium percarbonate materials have relatively good stability (Kingsfield Coated and Solvay Uncoated FB400). Each of these materials retained approximately 85% of its original peroxide content after 125 days of testing. Based on these stability results, these two commercial materials are preferred for use in the reduced weight DF-200 formulation.

Methods to Enhance the Dissolution Rate and Solubility of Sodium Percarbonate

However, there are two problems associated with the use of sodium percarbonate. First, it is slow to dissolve in solution and requires vigorous mixing (e.g., at its solubility limit of 12%, it may require several hours of mixing to completely dissolve). The second problem is that sodium percarbonate has a relatively low solubility limit. At its solubility limit, sodium percarbonate only yields a hydrogen peroxide concentration of ~3.6% (w/v) which is right at the lower limit required for effective DF-200 formulations. To overcome these problems, various "co-solvent" materials have been identified that, when dissolved in conjunction with sodium percarbonate, both increase the solubility and the rate of dissolution of the percarbonate. In general, these materials are inorganic potassium or ammonium salts. These materials, and some of their properties, are summarized in Table 4.

TABLE 4

Summary of sodium percarbonate co-solvent material properties

| Material | Required Concentration (w/v) to dissolve 20% (w/v) sodium percarbonate | Approximate Dissolution Time in De-ionized Water (minutes) | Compatible with Seawater | Comments |
|---|---|---|---|---|
| Potassium Sulfate | 12% | 10 | No | |
| Potassium Phosphate (dibasic) | 12% | 6 | No | |
| Potassium Citrate (tribasic) | 20% | 12 | Yes | Very slow dissolution in saltwater |
| Potassium Tetraborate Tetrahydrate | 4% | 5 | Yes | Precipitates from solution after ~4 hours |
| Ammonium Sulfate | 12% | 10 | No | Significant odor |

Various combinations of these materials were also investigated. After a series of experiments, it was determined that a combination of 4% (w/v) potassium tetraborate tetrahydrate and 8% (w/v) potassium citrate could be used to rapidly dissolve 20% (w/v) sodium percarbonate within approximately 5 minutes in both freshwater and saltwater. Addition of 8% (w/v) sorbitol prevents the precipitation of the potassium tetraborate. This combination of materials was used in the development of the reduced weight DF-200 formulation.

Reduced Weight Formulation Components

Reduced weight decontamination formulations of DF-200, according to the present invention, consist of the following components:

Part A: Solubilizing and Buffering ingredients;
   Part B: Solid Hydrogen Peroxide Material;
   Part C: Surfactant, Peroxide Activator, and Foam Stabilizing Ingredients; and
   Part D: Makeup Water—freshwater or saltwater supplied from a local source at the point of use.

A first example of a preferred formulation for decontamination of chemical and biological warfare agents is shown below:

Example #1

By Weight

Part A (Solubilizing and Buffering Ingredients)
20 g Potassium Tetraborate Tetrahydrate
40 g Potassium Citrate (Tribasic)
7 g Potassium Hydroxide
Part B (Solid Hydrogen Peroxide Material)
100 g Sodium Percarbonate (Solvay FB400)
Part C (Surfactant. Peroxide Activator, and Foam Stabilizing Ingredients)
5 g Glycerol Diacetate (Diacetin)
30 g Tetraacetyl Ethylene Diamine (Warwick B637)
11 g Dodecyl Trimethyl Ammonium Chloride
4 g Tripropylene Glycol Methyl Ether
2 g 1-Dodecanol
40 g Sorbitol (Sorbigem Fines)
Part D (Makeup Water)
500 g Water (Freshwater or Saltwater)
Example #1, converted to concentration, in terms of percentage by weight (wt %) of the made-up formulation:

Example #1

By weight %

Part A (Solubilizing and Buffering Ingredients)—Dry
2.6 wt % Potassium Tetraborate Tetrahydrate
5.3 wt % Potassium Citrate (Tribasic)
0.9 wt % Potassium Hydroxide
Part B (Solid Hydrogen Peroxide Material)—Dry
13.2 wt % Sodium Percarbonate (Solvay FB400)
Part C (Surfactant, Peroxide Activator, and Foam Stabilizing Ingredients)—Dry
0.7 wt % Glycerol Diacetate (Diacetin)
3.9 wt % Tetraacetyl Ethylene Diamine (Warwick B637)
1.4 wt % Dodecyl Trimethyl Ammonium Chloride
0.5 wt % Tripropylene Glycol Methyl Ether
0.3 wt % 1-Dodecanol
5.3 wt % Sorbitol (Sorbigem Fines)
Part D (Makeup Water)
65.8 wt % Water (Freshwater or Saltwater)
Total=99.9%
Reduced weight DF-200 formulations can be packaged, stored, and transported to the point of use in the form of a three-part kit (i.e., Parts A, B, and C, each packaged separately in individual containers). Then, at the point of use, the makeup water (Part D) is added.
To prepare Part C as a dry powder, suitable for packaging and storage, use the following:
1. Add glycerol diacetate to an empty vessel.
2. Add tripropylene glycol methyl ether. Stir until well mixed.
3. Add Dodecyl Trimethyl Ammonium chloride. Stir until dispersed throughout liquid and all lumps are dissolved.
4. Add 1-dodecanol. Stir (a paste will form).
5. Add tetraacetyl ethylene diamine. Stir (a paste will form).
6. Add sorbitol. A free flowing powder will result.
The addition of the first four ingredients in Part C results in the formation of a paste, which makes it easy to form a free-flowing powder upon the addition of the fifth and sixth ingredients. Adding the ingredients in different orders will work, but more sorbitol may need to be added to get a free-flowing powder.
It is possible to pre-mix all of the dry ingredients (A, B, and C) together, but the shelf-life of the product will be less because some of the ingredients may cause degradation of other ingredients (especially under high temperature storage). This is important for the military (to keep parts separate) but may be less important for a consumer-type product.
To prepare a made-up, reduced weight DF-200 formulation (i.e., ready to be applied to a contaminated surface), use the following method.
1. Add Part D (makeup water) to an empty vessel.
2. Add Part A. Stir vigorously until dissolved.
3. Add Part B. Stir vigorously until dissolved.
4. Reduce stirring speed. Add Part C. Stir gently until dissolved.
5. The formulation is ready for use.
Notes: The pH of the formulation should be between 9.6-10.10. The formulation should be used within six hours after mixing. Optimal deployment is through a compressed air foam generating system.
To make one gallon of made-up DF-200, using the reduced weight configuration, the following materials can be used:
Part A—Solubilizing Ingredients (borate and citrate)
    0.9 lb. per gallon
Part B—Solid Peroxide Material (sodium percarbonate)
    1.4 lb. per gallon
Part C—Foam Ingredients (surfactant, foam stabilizer, activator)
    1.2 lb. per gallon
Part D—Make-up Water
    6.7 lb. per gallon (0.8 gallons)
This requires 3.5 lbs of dry material to make one gallon of DF-200 (as compared to an 'All-liquid' version of DF-200 that weighs 8.97 lbs/gallon). Therefore, this represents a 61% weight savings over the standard 'all-liquid' configuration of DF-200.
Substitutions for various ingredients can be made. For example, the combination of potassium tetraborate tetrahyrate, potassium citrate, and potassium hydroxide in Part A can be replaced with potassium phosphate (dibasic), potassium sulfate, or potassium citrate alone (see Table 4). However, these ingredients do not provide the desired effect of increasing the dissolution rate and solubility of sodium percarbonate when saltwater is used as the makeup water (i.e., Part D). However, they could be used if the makeup water will always be freshwater.
In Part C, the solvent (tripropylene glycol methyl ether) can be replaced by other solvents such as hexylene glycol, diethylene glycol methyl ether, or propylene glycol. In addition, the surfactant can be replaced by other cationic surfactants, such as other types of quaternary ammonium compounds (e.g., benzyl dodecyldimethyl ammonium chloride, didecyldimethylammonium chloride), amine alkoxylates (e.g., polyethylene glycol cocoamine), and amine oxides (e.g., lauric dimethylamine oxide). However, it was determined through a series of tests, that Dodecyl Trimethyl Ammonium chloride provides superior efficacy as compared to other cationic surfactants; so it is considered to be a preferred surfactant for use in preferred formulations. Dodecyl Trimethyl Ammonium chloride also provides the best foam stability, as compared to other cationic surfactants. Sorbitol can also be replaced with mannitol (e.g., Mannigem Fines), or other sorbent materials (see below) with no effect on the formulation.

Sorbent Material Added to "Dry Out" Liquid Ingredients

A water-soluble, highly adsorbent additive is used to "dry out" one or more liquid ingredients of the family of DF-200 decontamination formulations, such as the liquid bleaching activator (i.e., peroxide activator) that is used for the "Part C" component of a multi-part, kit configuration (e.g., 3-part or 4-part configuration). A goal of "drying out" the liquid bleaching activator(s) is to produce a dry, free-flowing powder that can be placed in protective packaging with a desiccant, have an extended shelf life, be more convenient to handle and mix in the field (as compared to handling and mixing a liquid), and not leave a residue. In this way, the sorbent material acts as a drying agent.

The process of "drying out" the liquid bleaching activator (e.g., propylene glycol diacetate or glycerol diacetate), or other liquid components, is not really an evaporation process as it is commonly understood. Rather, the present invention uses a sorbent additive that absorbs and/or adsorbs (i.e., at room temperature) substantially all of the liquid activator to produce a powdered, free-flowing product that is easier to handle. The sorbent additive preferably does not contain any water, since most of the bleaching activators will hydrolyze or degrade in the presence of moisture. Also, the sorbent additive preferably should be water-soluble, so that it can be rapidly dissolved and mixed, and leave no residue.

Alternatively, an insoluble sorbent additive may be used (e.g., Cabosil), depending on the application, if the presence of insoluble particles in the formulation is acceptable. For example, insoluble sorbent particles may be used as a cleaning solution and/or where an abrasive effect is desired. Also, for some methods of application, the presence of a sludge at the bottom of a container may not be a problem. However, the presence of insoluble sorbent particles in the decontamination formulation may damage a pump mechanism, clog a spray nozzle, or leave an undesirable residue. The use of insoluble silica particles will also prevent the use of the formulation as an aqueous foam. If such particles are used, the formulation would be more suitably deployed as a liquid spray or a gel.

The sorbent additive is preferably finely ground to a small particle size so that a large effective surface area can be provided for adsorbing/absorbing the liquid activator. The sorbent additive preferably is chemically compatible with the DF-200 family of formulations, and should not cause degradation of the foaming properties and/or decontamination effectiveness. The sorbent additive may be selected from elements/ingredients already found in the DF-200 decontamination formulations. The sorbent additive may comprise a single powder, or a blend of different powders of different materials. For example, in some foaming embodiments of DF-200, Polyethlyene Glycol 8000 (PEG 8000 or Carbowax 8000) is used as a viscosity builder. Since the PEG 8000 used in the formulation presented herein is typically provided as a fine powder, and is essentially anhydrous, then it can also serve as some (or all) of the sorbent additive for "drying out" the liquid bleaching activator component.

Suitable compounds that may be used as the sorbent additive, either alone or in various combinations, according to the present invention, include, but are not limited to:
Sodium hexa meta phosphate $(NaPO_3)_6$
Sodium ortho phosphate $Na_3PO_4$
Sodium mono hydrogen ortho phosphate $Na_2HPO_4$
Sodium acid pyro phosphate $Na_4P_2O_7$
Sodium tri-polyphosphate $Na_5P_3O_{10}$
Sodium sulfate $Na_2SO_4$ (fine grind)
Sodium carbonate $Na_2CO_3$ (or bicarbonate)
Calcium meta phosphate $Ca(PO_3)_2$
Calcium hypo chlorite $Ca(ClO)_2$
Calcium chloride $CaCl_2$
Calcium carbonate $CaCO_3$
Potassium bicarbonate $KHCO_3$
Potassium bromide $KBr$
Potassium carbonate $K_2CO_3$
Zeolytes
Precipitated Silicas
Percarbonates
Sodium Citrate
Dendrite Salt (i.e., sea salt)
Citric Acid
Potassium Bromide
Polyethylene Glycols, PEG 8000
Urea
Polyols (e.g., Sorbitol, Mannitol, etc.)

Examples of suitable polyols that may be used as the sorbent additive of the present invention include, but are not limited to:
Sorbitol,
Mannitol,
Hydrogenated Starch Hydrolysates (HSH),
Maltitol,
Zylitol,
Lactitol Monohydrate,
Anhydrous Isomalt,
Erythritol, and
Polydextrose.

The polyols listed above are sugar-free sweeteners. They are carbohydrates, but they are not sugars. Chemically, polyols are considered polyhydric alcohols or "sugar alcohols" because part of the structure resembles sugar and part is similar to alcohols. However, these sugar-free sweeteners are neither sugars nor alcohols, as those word are commonly used. They are derived from carbohydrates whose carbonyl group (e.g., aldehyde or ketone, reducing sugar) has been reduced to a primary or secondary hydroxyl group.

The most widely used polyols in the food industry are sorbitol, mannitol, and malitol. Sorbitol is derived from glucose; mannitol from fructose; and malitol from high maltose corn syrup. Sorbogem™ and Mannogem™ are product names for sorbitol and mannitol sold by SPI Polyols, Inc., and are available in a wide range of particle size, down to fine sizes (i.e., Sorbogem Fines™).

Sorbitol is a hexahydric alcohol ($C_6H_{14}O_6$) corresponding to glucose, and has a molecular weight of 182.2. It occurs naturally, and is also produced by the hydrogenation of glucose syrup in the presence of Raney Nickel Catalyst. Some synonyms for sorbitol include: cholaxine, clucitol, diakarmon, gulitol, l-gulitol, karion, nivitin, sionit, sorbicolan, sorbite, d-sorbitol, sorbo, sorbol, sorbostyl, sorvilande. Sorbitol has a CAS No 50-70-4 and an EC No. 200-061-5. The sorbent additive may be selected to be a "G.R.A.S." material, meaning that it is Generally Accepted As Safe to be used in this and other applications.

Non-Foaming Gel Formulations

"Reduced weight" formulations have also been developed that can be deployed as a gel, instead of as a foam. These formulations make use of polymers or fumed silica materials to form a mixture that can remain on vertical surfaces or downward horizontal facing surfaces for more than 30 minutes after deployment. An example of a gel formulation is shown below:

Example #2

By Weight

Part A (Solid Solubilizing and Buffering Ingredients
20 g Potassium Tetraborate Tetrahydrate
40 g Potassium Citrate (Tribasic)
7 g Potassium Hydroxide
Part B (Solid Hydrogen Peroxide Material)
100 g Sodium Percarbonate (Solvay FB400)
Part C (Surfactant Peroxide Activator, and Gel Ingredients)
10 g Glycerol Diacetate (Diacetin)
30 g Tetraacetyl Ethylene Diamine (TAED)
11 g Dodecyl Trimethyl Ammonium Chloride (or Variquat 80MC, Adogen 477, Videt Q3)
20 g Sorbitol (Sorbigem Fines)
17.0 g Cabosil M5 (Fumed Silica)
Part D (Makeup Water)
500 g Water (Freshwater or Saltwater)

Example #2

By Weight %

Part A (Solid Solubilizing and Buffering Ingredients)
2.6 wt % Potassium Tetraborate Tetrahydrate
5.3 wt % Potassium Citrate (Tribasic)
0.9 wt % Potassium Hydroxide
Part B (Solid Hydrogen Peroxide Material)
13.2 wt % Sodium Percarbonate (Solvay FB400)
Part C (Surfactant, Peroxide Activator, and Gel Ingredients)
1.3 wt % Glycerol Diacetate (Diacetin)
4.0 wt % Tetraacetyl Ethylene Diamine (TAED)
1.5 wt % Dodecyl Trimethyl Ammonium Chloride (or Variquat 80MC, Adogen 477, Videt Q3)
2.6 wt % Sorbitol (Sorbigem Fines)
2.2 wt % Cabosil M5 (Fumed Silica)
Part D (Makeup Water)
66.2 wt % Water (Freshwater or Saltwater)

Low concentrations of certain polymers can be used in place of or in conjunction with the Cabosil fumed silica in the gel formulation above. Other fumed silica products or thixotropic materials may also be used. In this case, a polymer with a tolerance for a high ionic strength is required. A preferred polymer is Vanzan NF (xanthan gum), a high ionic strength tolerant polymer produced by R. T. Vanderbilt Company, Inc. The gel formulations can comprise at least 2 wt % fumed silica, or at least 0.05 wt % of zanthan gum.

A feature of these non-foaming formulations is that they can be easily deployed through off-the shelf equipment such as paint sprayers. They can also easily achieve the desired contact time on a surface of greater than 30 minutes. In addition, a greater selection of cationic surfactants can be used since the use of a surfactant with good foam stability (best achieved by Dodecyl Trimethyl Ammonium chloride) is not necessary. A disadvantage is that they cannot be deployed through the existing foam generating equipment that is used for the standard DF-200 formulation; and they require more vigorous means to clean-up after drying (e.g., rinsing or brushing).

Reduced weight DF-200 formulations can also be used for other disinfection and neutralization applications where the toxic chemical or biological compounds are less resistant and/or less toxic than chemical warfare agents such as GD, VX, or HD; or biological warfare agents such as anthrax spores. Examples of these "less-demanding" applications include: inactivation of viruses (e.g., avian influenza, smallpox, foot and mouth disease, etc.) or vegetative cells (e.g., *E. coli, salmonella*, etc.) or neutralization of toxic industrial chemicals (e.g., sodium cyanide). In this case, the concentrations of the ingredients of the formulation could be reduced, for example, in the ranges shown below in Example #3:

Example #3

By Weight

Part A
3-20 g Potassium Tetraborate Tetrahydrate
6-40 g Potassium Citrate (Tribasic)
1-7 g Potassium Hydroxide
Part B
15-100 g Sodium Percarbonate (Solvay FB400)
Part C
1-5 g Glycerol Diacetate (Diacetin)
5-30 g Tetraacetyl Ethylene Diamine (Warwick B637)
0-11 g Dodecyl Trimethyl Ammonium Chloride
0-4 g Tripropylene Glycol Methyl Ether
0-2 g 1-Dodecanol
6.7-40 g Sorbitol (Sorbigem Fines)
Part D
500 g Water Example #3, converted to concentration, in terms of percentage by weight (wt %) of the made-up formulation:

Example #3

By Weight %

Part A (Solubilizing and Buffering Ingredients)—Dry
0.6 wt % Potassium Tetraborate Tetrahydrate
1.1 wt % Potassium Citrate (Tribasic)
0.2 wt % Potassium Hydroxide
Part B (Solid Hydrogen Peroxide Material)—Dry
2.8 wt % Sodium Percarbonate (Solvay FB400)
Part C (Surfactant, Peroxide Activator, and Foam Stabilizing Ingredients)—Dry
0.2 wt % Glycerol Diacetate (Diacetin)
0.9 wt % Tetraacetyl Ethylene Diamine (Warwick B637)
0.0 wt % Dodecyl Trimethyl Ammonium Chloride
0.0 wt % Tripropylene Glycol Methyl Ether
0.0 wt % 1-Dodecanol
1.2 wt % Sorbitol (Sorbigem Fines)
Part D (Makeup Water)
92.9 wt % Water (Freshwater or Saltwater)
Total=99.9%

An example of a range of concentrations of ingredients of a reduced weight DF-200 formulation is shown in Example #4:

Example #4

By weight %

Part A (Solubilizing and Buffering Ingredients)—Dry
0.5-3 wt % Potassium Tetraborate Tetrahydrate
1-6 wt % Potassium Citrate (Tribasic)
0.2-1 wt % Potassium Hydroxide
Part B (Solid Hydrogen Peroxide Material)—Dry
2-15 wt % Sodium Percarbonate (Solvay FB400)
Part C (Surfactant Peroxide Activator and Foam Stabilizing Ingredients)—Dry
0.1-1 wt % Glycerol Diacetate (Diacetin)
0.5-5 wt % Tetraacetyl Ethylene Diamine (Warwick B637)

0-2 wt % Dodecyl Trimethyl Ammonium Chloride
0-1 wt % Tripropylene Glycol Methyl Ether
0-1 wt % 1-Dodecanol
1-6 wt % Sorbitol (Sorbigem Fines)
Part D (Makeup Water)
Balance—Water (Freshwater or Saltwater)
Total=100%

Efficacy Testing of the Reduced Weight DF-200 Formulation

The performance of a preferred reduced weight DF-200 configuration (formulation shown above in Example #1) for neutralization of chemical agent simulants, using deionized water as the make-up water (Part D), is shown in Table 5. These tests were conducted in a solution of DF-200 at a decon-to-stimulant ratio of 200:1. The results are compared to the standard "all-liquid" version of DF-200.

TABLE 5

Percent remaining simulant in solution tests of the reduced weight DF-200 configuration using deionized water as the make-up water.

| | VX Simulant | | | HD Simulant | | |
|---|---|---|---|---|---|---|
| Formulation | 1 Min. | 15 Min. | 60 Min. | 1 Min. | 15 Min. | 60 Min. |
| DF-200 (Standard All-Liquid) | 81.6 | ND | >99.9 | 67.6 | 98.6 | ND |
| Reduced Weight DF-200 (Dry -deionized water) | 98.3 | 99.8 | >99.9 | 93.8 | 97.8 | 99.5 |

The performance of a reduced weight DF-200 configuration (formulation shown above in Example #1) for neutralization of chemical agent simulants using deionized water and saltwater as the make-up water (Part D) is shown in Table 6. These tests were conducted on the surface of CARC (chemical agent resistant coating) at a decon-to-stimulant ratio of 200:1. Contact time was 30 minutes. The results are compared to the standard "all-liquid" version of DF-200.

TABLE 6

Percent remaining simulant in surface tests on CARC (chemical agent resistant coating) using the reduced weight DF-200 configuration with deionized water and saltwater as the make-up water. Simulant: decon ratio, 200:1. Contact time, 30 m.

| | VX Simulant | | HD Simulant | |
|---|---|---|---|---|
| Formulation | % Decon | % Decon on Surface | % Decon | % Decon on Surface |
| DF-200 (Standard.All-Liquid) | 87.3 | 99.0 | 79.4 | 89.0 |
| Reduced Weight DF-200 (Dry-deionized water) | 97.0 | 99.3 | 93.6 | 97.8 |
| Reduced Weight DF-200 (Dry-saltwater) | 96.5 | 99.3 | 90.4 | 97.0 |

Figure 3:
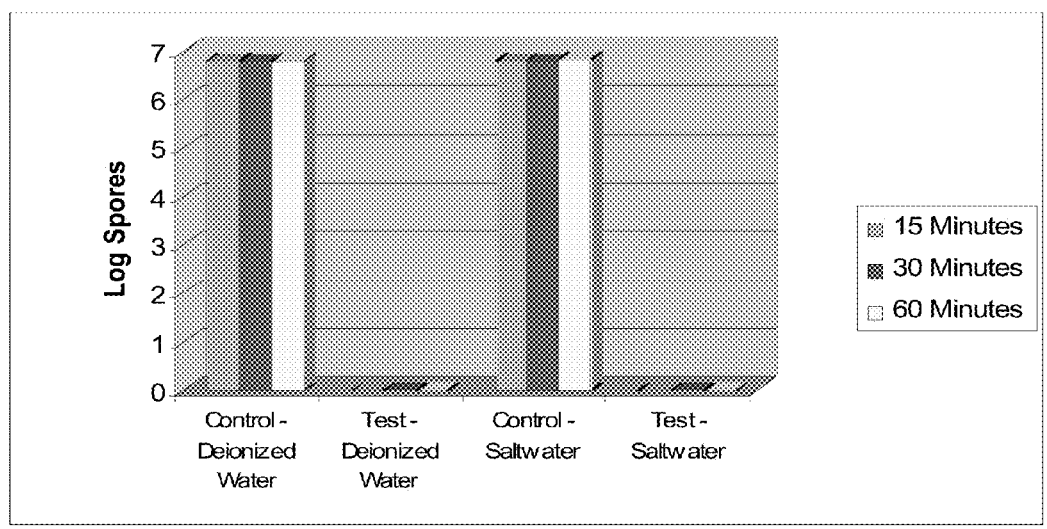
FIG. 3 shows a plot of spore count for different formulations.

Additionally, tests against the anthrax spore simulant (*Bacillus globigii* spores) demonstrated 99.9999% (7-log) kill after a 15, 30, and 60 minute exposure to the preferred reduced weight DF-200 formulation, using both deionized water and saltwater as the make-up water. The results are shown in FIG. 3.

Reduced Weight Versions using Liquid Hydrogen Peroxide

Two "reduced weight" versions of the Sandia DF-200 decontamination formulations have been developed that utilize a liquid hydrogen peroxide solution as the peroxide source. In each case, the formulations utilize solutions that contain slightly less than 20% hydrogen peroxide by weight. Keeping the concentration of hydrogen peroxide in these solutions less than 20% is important because it allows the solutions to be shipped on aircraft in rather large quantities making it practical for use by the military and other organizations. The US Department of Transportation (DOT) shipping regulations for hydrogen peroxide solutions are summarized in Table 7.

TABLE 7

Summary of shipping requirements for hydrogen peroxide solutions

| Peroxide Concentration | Hazard Class | Quantity Limit (per container) | |
|---|---|---|---|
| | | Passenger Air/Rail | Cargo Air |
| <8% | Non-hazardous | No restrictions | No restrictions |
| ≥8% but <20% | Class 5.1 Oxidizer | 2.5 L | 30 L |
| ≥20% but <40% | Class 5.1 Oxidizer | 1 L | 5 L |
| ≥40% but <60% | Class 5.1 Oxidizer | Forbidden | Forbidden |
| ≥60% | Class 5.1 Oxidizer | Forbidden | Forbidden |

A first reduced weight formulation that utilizes liquid hydrogen peroxide is shown below (Example #5). This formulation utilizes an aqueous hydrogen peroxide solution (19.9% hydrogen peroxide strength) as the peroxide source, instead of sodium percarbonate. The mixing order is D, A, C, B. Stabilized hydrogen peroxide solution can be used.

Example #5

By Weight

Part A (Dry)
50.0 g Sorbogem Crystalline Sorbitol (CAS: 50-70-4)
70.0 g Potassium Carbonate (CAS: 584-08-7)
4.0 g 1-Dodecanol (CAS: 112-53-8)
8.0 g Tripropylene Glycol Methyl Ether (CAS: 25498-49-1)
11.0 g Dodecyl Trimethyl Ammonium Chloride (solid)
Part B (Liquid)
170.0 g Stabilized Hydrogen Peroxide Solution (19.9% $H_2O_2$)
Part C (Liquid)
20.0 g Propylene Glycol (CAS: 57-55-6)
40.0 g Diacetin (CAS: 25395-31-7)
Part D (Make-Up Water)
500.0 g Water Example #5

By weight %

Part A (Dry)
5.7 wt % Sorbogem Crystalline Sorbitol (CAS: 50-70-4)
8.0 wt % Potassium Carbonate (CAS: 584-08-7)
0.5 wt % 1-Dodecanol (CAS: 112-53-8)
0.9 wt % Tripropylene Glycol Methyl Ether (CAS: 25498-49-1)
1.3 wt % Dodecyl Trimethyl Ammonium Chloride (solid)
Part B (Liquid)
19.5 wt % Stabilized Hydrogen Peroxide Solution (19.9% $H_2O_2$)
Part C (Liquid)
2.3 wt % Propylene Glycol (CAS: 57-55-6)
4.6 wt % Diacetin (CAS: 25395-31-7)
Part D (Make-Up Water)
57.3 wt % Water Example #5 consists of one solid component and two liquid components that are added to make-up water. To prepare the formulation, start with Part D (water). Add Part A and stir.

Add Part C and stir. Add Part B and stir. The pH of the formulation should be between 9.6-10.0 within 5 minutes after mixing. Note that the 1-dodecanol in this formulation is in Part A because placing the 1-dodecanol in Part C will cause this liquid to freeze near 7° C. There is sufficient solid material in Part A to sorb the 1-dodecanol and tripropylene glycol methyl ether to make it a free flowing powder. To prepare Part A, start with the tripropylene glycol methyl ether. Add the 1-dodecanol and mix. Add the surfactant and mix until a paste is formed. Add Sorbogem Fines and potassium carbonate and mix to form a free flowing powder. This reduced weight formulation weighs approximately 40% of the standard DF-200 formulation.

Another reduced weight formulation that utilizes liquid hydrogen peroxide is shown below in Example #6. This formulation also utilizes a 19.9% hydrogen peroxide solution as the source of hydrogen peroxide, instead of sodium percarbonate.

Example #6

By Weight

Part A (Dry)
30.0 g Sorbogem Crystalline Sorbitol (CAS: 50-70-4)
60.0 g Potassium Carbonate (CAS: 584-08-7)
Part B (Liquid)
170.0 g 19.9% Stabilized Hydrogen Peroxide Solution
Part C (Dry)
11.0 g Dodecyl trimethyl ammonium chloride (in powdered form)
40.0 g Tetra-acetyl Ethylenediamine (TAED)
2.0 g 1-Dodecanol (CAS: 112-53-8)
4.0 g Propylene Glycol (CAS: 57-55-6)
20.0 g Sorbogem Crystalline Sorbitol (CAS: 50-70-4)
Part D (Make-Up Water)
500.0 g Water

Example #6

By Weight %

Part A (Dry)
3.6 wt % Sorbogem Crystalline Sorbitol (CAS: 50-70-4)
7.2 wt % Potassium Carbonate (CAS: 584-08-7)
Part B (Liquid)
20.3 wt % Stabilized Hydrogen Peroxide Solution (19.9% $H_2O_2$)
Part C (Dry)
1.3 wt % Dodecyl trimethyl ammonium chloride (in powdered form)
4.8 wt % Tetra-acetyl Ethylenediamine (TAED)
0.2 wt % 1-Dodecanol (CAS: 112-53-8)
0.5 wt % Propylene Glycol (CAS: 57-55-6)
2.4 wt % Sorbogem Crystalline Sorbitol (CAS: 50-70-4)
Part D (Make-Up Water)
59.7 wt % Water Example #6 consists of two solid components and one liquid component that are added to make-up water. To mix this formulation, start with Part D (water). Add Part A and stir until dissolved. Add Part C and stir. Add Part B and stir until all solids are dissolved. The pH of the formulation should be between 9.6-10.0 within 5 minutes after mixing. To prepare Part C, start with the propylene glycol. Add the dodecanol and mix. Add the dodecyl trimethyl ammonium chloride and mix. Add the TAED and stir until a powder is formed. Add the Sorbogem/Sorbitol until a free flowing powder results. More or less Sorbogem/Sorbitol can be used depending how much or little is required to construct a free flowing powder. This reduced weight formulation weighs approximately 40% of the standard DF-200 formulation.

A feature of using liquid hydrogen peroxide, instead of sodium percarbonate, in reduced weight formulations is that these formulations require much less mixing in order to prepare the formulations for use in the field. A disadvantage is that less weight savings are achieved, as compared to formulations that use sodium percarbonate.

Reduced weight formulations using liquid hydrogen peroxide have also been developed that can be deployed as a gel, instead of as a foam. These formulations make use of polymers or fumed silica materials to form a mixture that can remain on vertical surfaces or downward horizontal facing surfaces for more than 30 minutes after deployment. Examples #7 and 8 show gel formulations using hydrogen peroxide:

Example #7

By Weight

Part A (Dry)
70.0 g Potassium Carbonate (CAS: 584-08-7)
11 g Dodecyl Trimethyl Ammonium Chloride (or Variquat 80MC, Adogen 477, Videt Q3)
17.0 g Cabosil M5 (fumed silica)
Part B (Liquid)
170.0 g Stabilized Hydrogen Peroxide Solution (19.9% $H_2O_2$)
Part C (Liquid)
20.0 g Propylene Glycol (CAS: 57-55-6)
40.0 g Diacetin (CAS: 25395-31-7)
Part D (Make-Up Water)
500.0 g Water

Example #7

By Weight %

Part A (Dry)
8.5 wt % Potassium Carbonate (CAS: 584-08-7)
1.3 wt % Dodecyl Trimethyl Ammonium Chloride (or Variquat 80MC, Adogen 477, Videt Q3)
2.0 wt % Cabosil M5 (fumed silica)
Part B (Liquid)
20.5 wt % Stabilized Hydrogen Peroxide Solution (19.9% $H_2O_2$)
Part C (Liquid)
2.4 wt % Propylene Glycol (CAS: 57-55-6)
4.8 wt % Diacetin (CAS: 25395-31-7)
Part D (Make-Up Water)
60.3 wt % Water

Example #8

By Weight

Part A (Solid Buffering Ingredients)
60.0 g Potassium Carbonate (CAS: 584-08-7)
Part B (Liquid Hydrogen Peroxide Solution)
170.0 g Stabilized Hydrogen Peroxide Solution (19-9% $H_2O_2$)

Part C (Solid Surfactant Peroxide Activator, and Gel Ingredients)
11.0 g Dodecyl trimethyl ammonium chloride (or Variquat 80MC, Adogen 477, Videt Q3)
10.0 g Glycerol Diacetate (Diacetin)
30.0 g Tetra-acetyl Ethylenediamine (TAED)
17.0 g Cabosil M5 (Fumed Silica)
Part D (Make-Up Water)
500.0 g Water Example #8

By Weight %

Part A (Solid Buffering Ingredients)
7.5 wt % Potassium Carbonate (CAS: 584-08-7)
Part B (Liquid Hydrogen Peroxide Solution)
21.2 wt % Stabilized Hydrogen Peroxide Solution (19.9% $H_2O_2$)
Part C (Solid Surfactant, Peroxide Activator, and Gel ingredients)
1.4 wt % Dodecyl trimethyl ammonium chloride (or Variquat 80MC, Adogen 477, Videt Q3)
1.3 wt % Glycerol Diacetate (Diacetin)
3.7 wt % Tetra-acetyl Ethylenediamine (TAED)
2.1 wt % Cabosil M5 (Fumed Silica)
Part D (Make-Up Water)
62.5 wt % Water The particular examples discussed above are cited to illustrate particular embodiments of the invention. Other applications and embodiments of the apparatus and method of the present invention will become evident to those skilled in the art. It is to be understood that the invention is not limited in its application to the details of construction, materials used, and the arrangements of components set forth in the following description or illustrated in the drawings.

The scope of the invention is defined by the claims appended hereto.

What is claimed is:

1. A decontamination formulation, comprising, by weight percentage the following ingredients:
   0.5-3 wt % Potassium Tetraborate Tetrahydrate;
   1-6 wt % Potassium Citrate;
   0.2-1 wt % Potassium Hydroxide;
   2-15 wt % Sodium Percarbonate;
   0.1-1 wt % Glycerol Diacetate;
   0.5-5 wt % Tetraacetyl Ethylene Diamine;
   0-2 wt % Dodecyl Trimethyl Ammonium Chloride;
   0-1 wt % Tripropylene Glycol Methyl Ether;
   0-1 wt % 1-Dodecanol;
   1-6 wt % Sorbitol fines; and
   Water (remaining balance);
   wherein a combined amount of the potassium tetraborate tetrahydrate ingredient and the potassium citrate ingredient are selected to dissolve the sodium percarbonate ingredient of the water.

2. The decontamination formulation of claim 1, wherein the ingredients of the formulation are pre-packaged as a four-part kit, comprising all-dry Parts A, B, and C; to be mixed with Part D (water) in the field at the point of use, wherein:
   Part A (dry) comprises:
      the Potassium Tetraborate Tetrahydrate ingredient,
      the Potassium Citrate ingredient, and
      the Potassium Hydroxide ingredient;
   Part B (dry) comprises:
      the Sodium Percarbonate ingredient;
   Part C (dry) comprises:
      the Glycerol Diacetate ingredient,
      the Tetraacetyl Ethylene Diamine ingredient,
      the Dodecyl Trimethyl Ammonium Chloride ingredient,
      the Tripropylene Glycol Methyl Ether ingredient,
      the 1-Dodecanol ingredient, and
      the Sorbitol fines ingredient; and
   Part D comprises the water ingredient.

3. The decontamination formulation of claim 1, comprising, by weight percentage:
   0.6 wt % Potassium Tetraborate Tetrahydrate;
   1.1 wt % Potassium Citrate;
   0.2 wt % Potassium Hydroxide;
   2.8 wt % Sodium Percarbonate;
   0.2 wt % Glycerol Diacetate;
   0.9 wt % Tetraacetyl Ethylene Diamine;
   0 wt % Dodecyl Trimethyl Ammonium Chloride;
   0 wt % Tripropylene Glycol Methyl Ether;
   0 wt % 1-Dodecanol;
   1.2 wt % Sorbitol fines; and
   93 wt % Water.

4. The decontamination formulation of claim 1, comprising, by weight percentage:
   2.6 wt % Potassium Tetraborate Tetrahydrate;
   5.3 wt % Potassium Citrate;
   0.9 wt % Potassium Hydroxide;
   13.2 wt % Sodium Percarbonate;
   0.7 wt % Glycerol Diacetate;
   3.9 wt % Tetraacetyl Ethylene Diamine;
   1.4 wt % Dodecyl Trimethyl Ammonium Chloride;
   0.5 wt % Tripropylene Glycol Methyl Ether;
   0.3 wt % 1-Dodecanol;
   5.3 wt % Sorbitol fines; and
   65.8 wt % Water.

5. The decontamination formulation of claim 1, wherein the pH of the formulation is between 9.6 and 10.1.

6. The decontamination formulation of claim 1, wherein the ingredients of the formulation are pre-packaged as a four-part kit, comprising all-dry Parts A, B, and C; to be mixed with Part D (water) in the field at the point of use, wherein:
   Part A (dry) consists essentially of:
      the Potassium Tetraborate Tetrahydrate ingredient,
      the Potassium Citrate ingredient, and
      the Potassium Hydroxide ingredient;
   Part B (dry) consists essentially of:
      the Sodium Percarbonate ingredient;
   Part C (dry) consists essentially of:
      the Glycerol Diacetate ingredient,
      the Tetraacetyl Ethylene Diamine ingredient,
      the Dodecyl Trimethyl Ammonium Chloride ingredient,
      the Tripropylene Glycol Methyl Ether ingredient,
      the 1-Dodecanol ingredient, and
      the Sorbitol fines ingredient; and
   Part D consists essentially of the water ingredient.

7. The decontamination formulation of claim 1, consisting essentially of, by weight percentage:
   0.6 wt % Potassium Tetraborate Tetrahydrate;
   1.1 wt % Potassium Citrate;
   0.2 wt % Potassium Hydroxide;
   2.8 wt % Sodium Percarbonate;
   0.2 wt % Glycerol Diacetate;
   0.9 wt % Tetraacetyl Ethylene Diamine;
   0 wt % Dodecyl Trimethyl Ammonium Chloride;
   0 wt % Tripropylene Glycol Methyl Ether;
   0 wt % 1-Dodecanol;
   1.2 wt % Sorbitol fines; and
   93 wt % Water.

8. The decontamination formulation of claim 1, consisting essentially of, by weight percentage:
- 2.6 wt % Potassium Tetraborate Tetrahydrate;
- 5.3 wt % Potassium Citrate;
- 0.9 wt % Potassium Hydroxide;
- 13.2 wt % Sodium Percarbonate;
- 0.7 wt % Glycerol Diacetate;
- 3.9 wt % Tetraacetyl Ethylene Diamine;
- 1.4 wt % Dodecyl Trimethyl Ammonium Chloride;
- 0.5 wt % Tripropylene Glycol Methyl Ether;
- 0.3 wt % 1-Dodecanol;
- 5.3 wt % Sorbitol fines; and
- 65.8 wt % Water.

9. The decontamination formulation of claim 1, further comprising a sufficient amount of fumed silica or xanthan gum so that the formulation can remain on vertical surfaces or downward horizontal facing surfaces for more than 30 minutes after deployment.

10. The decontamination formulation of claim 9, wherein the sufficient amount of fumed silica is at least 2 wt %.

11. The decontamination formulation of claim 9, wherein the sufficient amount of xanthan gum is at least 0.05 wt %.

* * * * *